United States Patent [19]

Jamison et al.

[11] Patent Number: 4,748,849

[45] Date of Patent: Jun. 7, 1988

[54] APPARATUS FOR DYNAMICALLY MEASURING FLUID LOSS CHARACTERISTICS

[75] Inventors: Dale E. Jamison, Humble; James V. Fisk, Houston, both of Tex.

[73] Assignee: NL Industries, Inc., New York, N.Y.

[21] Appl. No.: 10,684

[22] Filed: Feb. 4, 1987

[51] Int. Cl.$^4$ ............................................. G01N 15/04
[52] U.S. Cl. ..................................................... 73/61.4
[58] Field of Search ............................... 73/61.4, 61 R

[56] References Cited

U.S. PATENT DOCUMENTS

| 3,289,467 | 12/1966 | Parker et al. | 73/61.4 |
| 4,184,952 | 1/1980 | Stewart | 73/61 R |
| 4,397,177 | 8/1983 | Cain | 73/61.4 |
| 4,538,452 | 9/1985 | Hrvojic | 73/61.4 |
| 4,610,158 | 9/1986 | Lawton, Jr. | 73/61.4 |

FOREIGN PATENT DOCUMENTS 1363793  8/1974  United Kingdom ................. 73/61.4

Primary Examiner—Michael J. Tokar
Assistant Examiner—Joseph W. Roskos
Attorney, Agent, or Firm—Browning, Bushman, Zamecki & Anderson

[57] ABSTRACT

An apparatus for testing fluid loss characteristics of a test fluid such as drilling mud under static or dynamic conditions, the apparatus having a filter medium cell which has a generally vertically disposed cylindrical wall, the apparatus further including a first chamber which is in open communication with the inner surface of the cylindrical wall and a second chamber which is in communication with the outer surface of the cylindrical wall, there being a generally vertically disposed rotatable shaft which is received internally of the cylindrical wall, the shaft being driven by a motor or the like, the apparatus being capable of providing a differential pressure across the cylindrical wall such that fluid will flow from the first chamber to the second chamber in response to the differential pressure and the liquid passing into the second chamber can be suitably measured and used to calculate fluid loss rate of the test fluid.

11 Claims, 3 Drawing Sheets

APPARATUS FOR DYNAMICALLY MEASURING FLUID LOSS CHARACTERISTICS

BACKGROUND OF THE INVENTION

1. Field of the Invention

The present invention relates to an apparatus for measuring fluid loss characteristics and, more particularly, to an apparatus for dynamically testing fluid loss characteristics of test fluids such as drilling fluids.

2. Description of the Prior Art

The drilling fluid, commonly referred to as drilling mud, used in the drilling of oil and gas wells, serves a number of purposes such as lubricating the bit, removing the cuttings from the borehole, etc. To accomplish its purposes, the drilling mud should, ideally, possess certain characteristics. For one, it should be capable, if desired, of depositing a coating on the wall of the borehole, the coating being commonly referred to as a filter cake. The filter cake serves to stabilize the borehole and prevent loss of the liquid portion of the drilling mud through the walls of the borehole into the adjoining formations. This loss of liquid from the drilling mud commonly referred to as fluid loss is a function of many variables such as the composition of the drilling mud, the types of formations encountered in the drilling process, temperatures and pressures in the borehole, etc.

It has long been the desire to be able to test drilling muds under simulated borehole conditions in an attempt to determine characteristics such as fluid loss. For example, British Pat. No. 1,363,793 discloses an apparatus for determining dynamic fluid loss trends in drilling fluids while U.S. Pat. No. 4,538,452 discloses an apparatus for measuring filter cake qualities of a drilling fluid under dynamic conditions.

Neither of the two cited patents, nor any of the other prior art known to Applicant, discloses an apparatus for dynamically testing the fluid loss characteristics of a drilling fluid or the like which can simulate borehole conditions such as high temperature and high pressure together with a simulation of the shearing action experienced by the drilling fluid during the actual drilling operation.

SUMMARY OF THE INVENTION

It is therefore an object of the present invention to provide an apparatus for dynamically testing fluid loss characteristics of a test fluid such as drilling mud.

Another object of the present invention is to provide an apparatus for dynamically testing drilling fluids in which borehole conditions such as high temperature, high pressure and shearing action resulting from rotation of the drill string are simulated.

The above and other objects of the present invention will become apparent from the drawings, the description given herein and the appended claims.

The dynamic test apparatus of the present invention comprises a filter medium cell having a generally vertically disposed, cylindrical wall section, the wall section being provided with an inner surface and an outer surface. At least part and preferably all of the wall section is formed of a filter medium. There are means defining a first chamber for a test fluid, the first chamber being in open communication with the inner surface of the cylindrical wall section of the cell. A second chamber defining means defines a second chamber which is in open communication with the outer surface of the cylindrical wall section of the cell. At least partially received in the filter medium cell is a generally vertically disposed rotatable shaft means, there being means provided to rotate the shaft. The apparatus further includes a means to apply a differential pressure across at least a portion of the cylindrical wall means between the first chamber and the second chamber through the filter medium portion of the wall section. Optionally, there are means to measure the amount of test fluid which passes from the first chamber to the second chamber through at least the filter medium part of the wall section in response to the differential pressure.

DESCRIPTION OF THE PREFERRED EMBODIMENT

While the invention will be described with reference to the testing of drilling fluids or drilling muds, it is to be understood that it is not so limited. The apparatus of the present invention can be used whenever it is desired to dynamically test the tendency of a fluid to pass through an at least partially permeable substrate.

Figure 1:
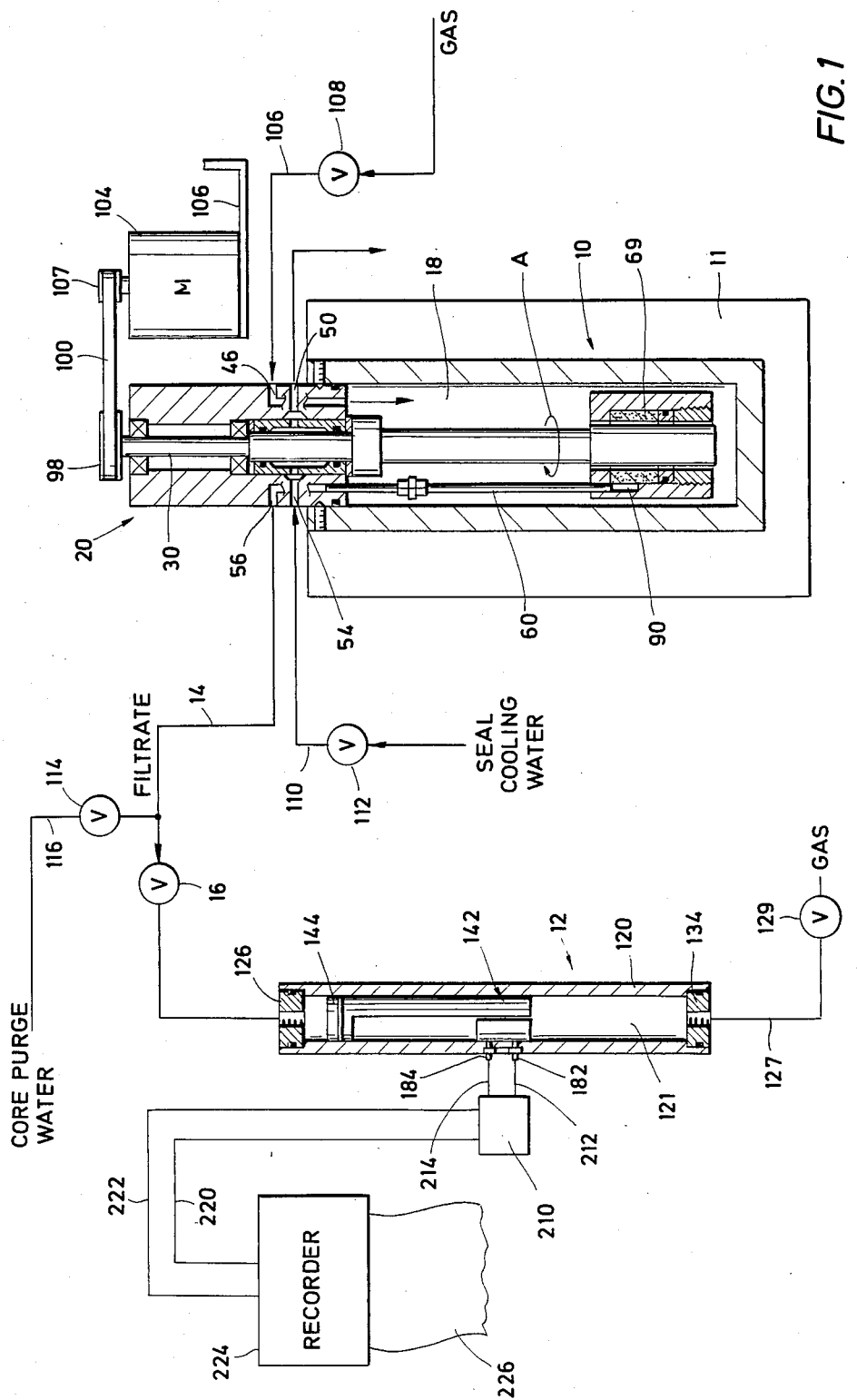
FIG. 1 is a diagrammatic view of the apparatus of the present invention, parts of the apparatus being shown in elevational cross section.

Referring first to FIG. 1, the apparatus of the present invention is comprised of two main components, a filtration unit, shown generally as 10, and a measuring unit, shown generally as 12. Units 10 and 12 are connected by a line 14 which provides fluid communication, in a manner described hereafter, between the filtration unit 10 and the measuring unit 12.

Figure 2:
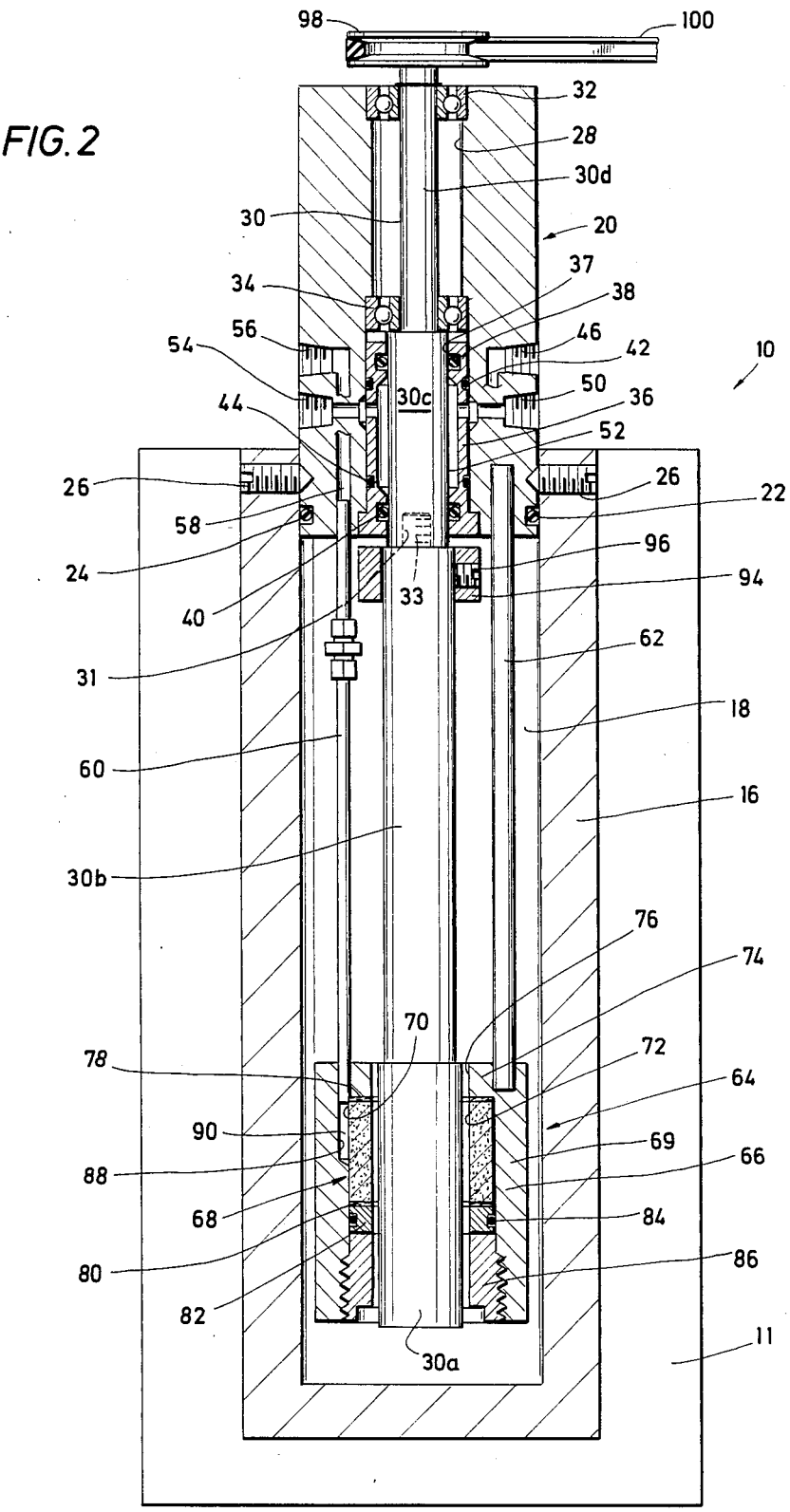
FIG. 2 is an elevational view, partly in section, of the filtration unit of the present invention.
Figure 3:
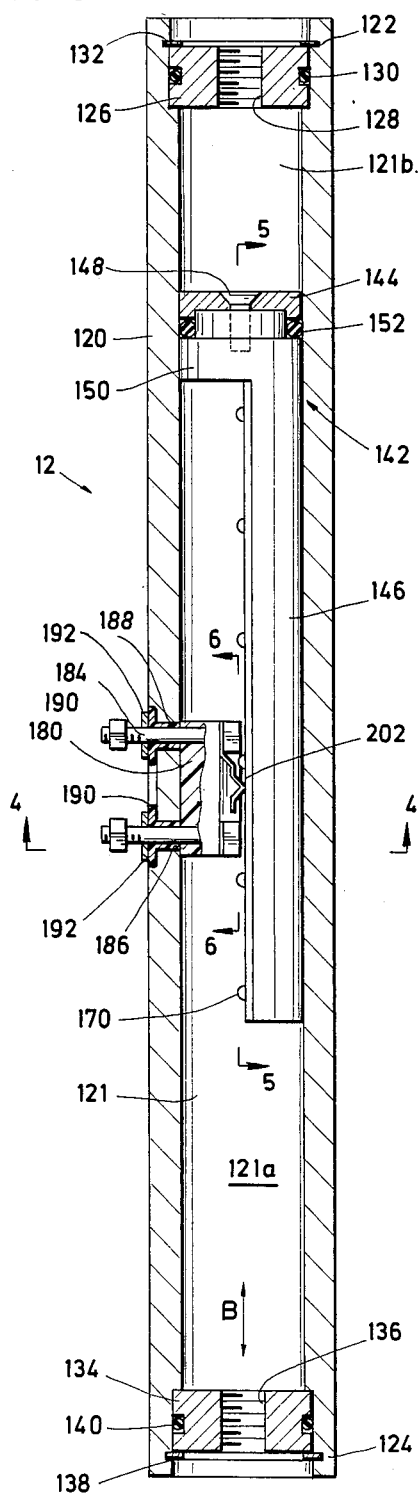
FIG. 3 is an elevational view, partly in section, of the measuring unit of the apparatus of the present invention.

The filtration unit 10, as best seen with reference to FIGS. 1 and 2, includes a generally cylindrical housing 16 partially defining an interior chamber 18. A heating jacket 11 surrounds housing 16 such that housing 16 and hence anything therein can be raised to a desired elevated temperature. Chamber 18 is also partially defined by a generally cylindrical cap, shown generally as 20, which is received in the open end of housing 16. To effect a seal between cap 20 and housing 16, thereby effectively sealing off chamber 18, an O-ring 22 is provided, O-ring 22 being carried in an annular groove 24 formed on the exterior surface of cap 20. To secure cap 20 to housing 16, locking screws 26 extend through threaded bores in the cylindrical wall of housing 16 and engage registering bores in the outer surface of cap 20.

A bore 28 extends longitudinally through cap 20. Received through bore 28 is a shaft 30, shaft 30 being journaled in bore 28 by means of upper and lower bearing assemblies 32 and 34, respectively. As can be seen, shaft 30 is multi-diameter along its length, the smallest diameter portion 30d of shaft 30 being journaled in bearings 32 and 34. Also received in bore 28 is a generally cylindrical O-ring carrier 36 having a bore 37 through which portion 30c of shaft 30 extends. O-ring carrier 36 serves to support radially inner, upper and lower O-ring 38 and 40, respectively, and radially outer, upper and lower O-rings 42 and 44, respectively. Thus, both shaft 30 and the bore 28 of cap 20 are sealed against fluid flow out of chamber 18.

Cap 20 is provided with a first fluid port 46 which communicates with a bore 48 (see FIG. 1) in cap 30 which in turn opens into chamber 18. A second fluid port 50 in cap 20 communicates with an annular chamber 52 formed partially by carrier 36 and in generally surrounding relationship to shaft 30. A third fluid port 54, diametrically opposite port 50, also communicates with chamber 52. A fourth fluid port 56 in cap 20 communicates with a bore 58 in cap 20 which in turn is in open communication with a flow tube 60 extending downwardly from cap 20 into chamber 18.

A support rod 62 is secured to cap 20 and extends downwardly into chamber 18. Support rod 62 is also secured to a filter medium support 64 disposed in chamber 18. As can be seen with reference to FIG. 2, tubing 60 is also secured to support 64. Thus, support 64 is substantially rigidly suspended in chamber 18 by means of rod 62 and flow tube 60. Support 64, which is generally cylindrical, has a generally cylindrical wall 66 which is substantially vertically aligned. Received internally of support 64 is a filter medium cell 68 which has a generally cylindrical wall 69 having an outer cylindrical surface 70 and an inner cylindrical surface 72. At least a portion, and preferably all, of the wall 69 is formed of a material which is at least partially permeable to liquids, particularly under pressure. Such materials include, without limitation, sintered metals, layered screens, natural mineral materials, synthetic materials, etc. The inner surface of wall 66 of support 64 is sized so as to generally snugly receive filter medium cell 68. Support 64 includes a flange 74 having a central bore 76 therethrough. An annular seal 78 effects a seal between the upper end of filter medium cell 68 and flange 74. A second annular seal 80 abuts the opposite end of filter medium cell 68. A bushing 82 carrying an O-ring 84 on its outer surface is held against seal 80 by means of a threaded plug 86 received in the bottom, open threaded end of support 64. The inner surface of wall 66 of support 64 has a radially outwardly extending recess 88 which forms a chamber 90 between the outer surface 70 of filter medium cell 68 and the inner surface of wall 66 of support 64. Chamber 90, as can be seen, is in open communication with flow tube 60. It will be appreciated that because of seals 78, 80, 84 and the upward pressure applied by threaded plug 86, chamber 90 is effectively sealed from chamber 18, save for any transfer of fluid which can occur through the filter medium material forming the cylindrical wall of filter medium cell 68 which is between chamber 18 and chamber 90.

Shaft 30, which also extends in a generally vertical disposition downwardly into chamber 18, has an enlarged lowermost portion 30a which is received through aperture 76 in flange 74 of support 64 and which is generally concentrically disposed with respect to filter medium cell 68. As shown, there is an annular clearance 92 between the outer surface of portion 30a of shaft 30 and the inner surface 72 of filter medium cell 68. Clearance 92, as is apparent, is in open communication with and forms a part of chamber 18. Shaft 30 is desirably of two-piece construction, one piece being formed by portions 30a and 30b, the other piece being formed by portions 30c and 30d. To connect the two pieces into a unitary body, the lowermost end of portion 30c is provided with a threaded bore 31 while the uppermost end of portion 30b is provided with a threaded stub shaft 33 which is threadedly received in bore 31. This permits the diameter of portion 30a to be varied to thereby vary the clearance 92 simply by changing the lowermost piece of shaft 30 comprised of portions 30a and 30b.

An annular slinger 94 is secured to portion 30b of shaft 30 at a position displaced upwardly from enlarged lower end 30a of shaft 30 and just below cap 20. Slinger 94 is secured to shaft 30 to rotate therewith by means of a set screw 96 extending through a bore in slinger 94 and engaging the outer surface of shaft 30. Slinger 94 serves the purpose of diverting the test fluid from away from cap 20 and hence away from the O-ring seals in carrier 36.

Referring now to FIG. 1, it can be seen that the vertically uppermost part of shaft 30 projects out of cap 20 and is secured to a pulley 98. Pulley 98, and hence shaft 30, are driven by a drive belt 100 which is received on a pulley 102 of a drive motor 104 suitably supported on a bracket or the like 103. Accordingly, when motor 104 is running, shaft 30 is caused to rotate in the direction shown by arrow A.

A fluid conduit 108 communicates with port 46 through a valve 108 to a source of pressurized gas (not shown). It will thus be appreciated that pressure can be applied through conduit 106, port 46, bore 48 and thereby pressure the interior chamber 18 in housing 16. To cool O-rings and carrier 36, cooling water is supplied via conduit 110 through valve 112 into port 54 and chamber 52 and then out of chamber 52 via port 50.

As earlier noted, chamber 90 is in open communication with port 56 by means of flow tube 60 and bore 58 in cap 20. Conduit 14 is also in open communication with port 56 and with measuring unit 12 via valve 16. Also connected to line 14 through valve 114 is a conduit 116 leading to a source of cold purge water. It will now be seen that with a test fluid, e.g. a drilling liquid or mud, received in chamber 18, if pressure is applied to chamber 18 via conduit 106, liquid permeating through the wall 69 of filter medium cell 68 will enter chamber 90, i.e. the liquid will pass from chamber 18 to chamber 90, will then be forced up tube 60, out port 56 into line 14 through valve 16 and into measuring unit 12.

Referring now to FIGS. 3-6, the measuring unit 12 is shown in greater detail. Measuring unit 12 comprises a generally cylindrical tube 120 having a first end 122 and a second end 124 and defining a piston chamber 121. Received in the first end 122 of tube 120 is a first plug 126 having a central, fluid port 128 whereby a tubing fitting or the like can be received to connect port 128 to conduit 14. Sealing between plug 126 and tube 120 is provided by an O-ring 130. Plug 126 is retained in the first end 122 of tube 120 by means of a snap ring 132. A second plug 134 is received in the second end 124 of tube 120, plug 134 having a central, fluid port 136. Port 136 allows connection to a source of pressurized gas (not shown) via line 127 and valve 129. A snap ring 138 retains plug 134 in tube 120, sealing between tube 120 and plug 134 being provided by an O-ring 140.

Figure 4:
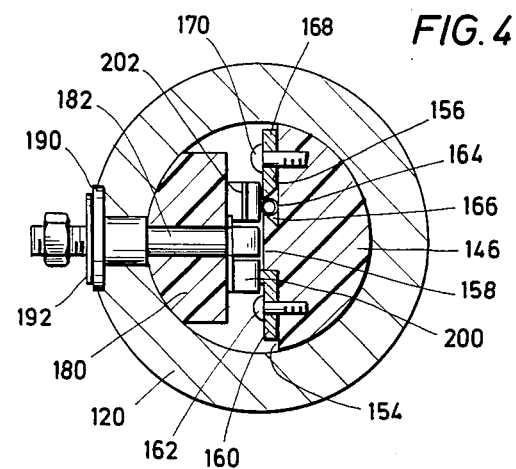
FIG. 4 is a view taken along the lines 4—4 of FIG. 3.
Figure 5:
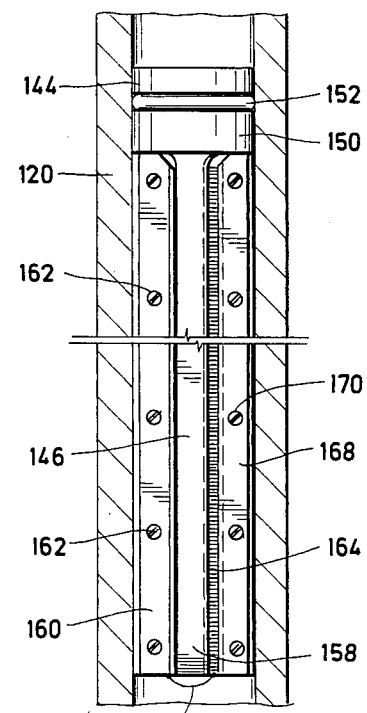
FIG. 5 is a view taken along the lines 5—5 of FIG. 3.
Figure 6:
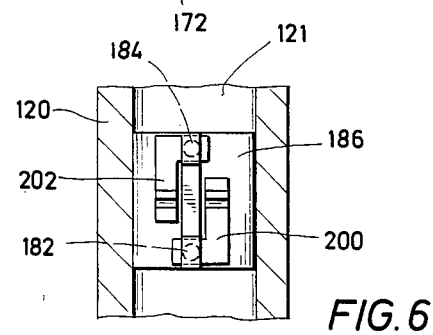
FIG. 6 is a view taken along the lines 6—6 of FIG. 3.

Slidably mounted internally of tube 120 is a piston assembly shown generally as 142. Piston assembly 142 comprises a piston cap 144 which is secured to a piston head 150 by means of a bolt 148 received in a threaded bore in the piston head 150 of piston 142. An annular seal ring 152 provides sealing between the tube 120 and the head 150 of piston 142 thereby dividing chamber 121 into two separate chambers 121a and 121b. As best seen in FIG. 4, piston 142 has a leg portion 146 which extends from head 150 along the length of tube 120 in chamber 121a and which is generally semi-circular when viewed in transverse cross section. Leg 146 has a first, longitudinally extending relief portion 154 and a second, longitudinally extending relief portion 156, relief portions 154 and 156 being laterally spaced by an upset portion 158 of leg 146. As can be seen, leg 146 and head 150 of piston 142 are formed of a plastic, and in any event an electrically non-conductive material. Mounted on relief 154 is an elongated conductive strip 160, strip 160 being secured to leg 146 by means of a series of screws 162. Mounted on relief 156 is an elongate coil 164 of a material whose electrical resistance varies with length. Coil 164 is received in an elongate undercut channel 166 formed in upset portion 158. To secure coil 166 to relief surface 156, a non-conductive, preferably plastic, strip 168 is secured to relief 166 by screws 170, coil 164 being effectively trapped in channel 166 between upset portion 158 and non-conductive strip 168. As best seen with reference to FIG. 5, conductive strip 160, which can be brass or the like, is electrically connected to coil 164 by means of a jumper wire 172. A contact support block 180 of a non-conductive material, e.g. plastic, is supported in chamber 121 by means of electrically conductive bolts 182 and 184 which extend through bores 186 and 188, respectively, formed in the wall of cylindrical tube 120. Bolts 182 and 184 extend through insulator/seals 190, bolts 182 and 184 being securely held in the wall of cylindrical tube 120 by lock nuts 192. Insulator seals 190 ensure that no gas leakage can occur out of chamber 121 through the bores 186 or 188 and electrically insulate bolts 182 and 184 from tube 120.

A first spring contact 200 is secured to block 180 by the head of bolt 182. A second spring contact 202 is secured to block 180 by the head of bolt 184. As best seen with reference to FIGS. 3 and 4, when the piston assembly 142 is mounted in tube 120, first contact 202 will engage resistance coil 164 while second contact 200 will engage conductive strip 160. Accordingly, there will be an electrically conductive path formed from bolt 182 to bolt 184 through conductive strip 160, jumper wire 172, resistance coil 164, and contact 200. More importantly, the resistance of the path will vary linerally as a function of the position of contact 202 on coil 164.

Referring now to FIG. 1, a circuit 210 which converts resistance to voltage is electrically connected to bolts 182 and 184 by means of conductors 212 and 214, respectively. It will be appreciated that as the piston assembly 142 moves through the piston chamber 121 in either direction as shown by arrow B, contact 202 will engage resistance coil 164 at different points along its length providing a corresponding resistance. By converting this resistance to a voltage signal, and with proper calibration, the position of piston assembly 142 can be accurately correlated with the voltage signal received from the circuit 210. Stated another way, the voltage signal received from circuit 210 can be directly related to how far piston assembly 142 has been displaced from end 122 of cylindrical tube 120, i.e. the volume increase of chamber 121b.

The voltage signal from circuit 210 is sent via conductors 220 and 222 to a recorder 224 or other such readout device which gives a display, shown here in the form of chart paper 226, the chart paper 226 conveniently indicating the volume displacement of piston assembly 142 as a function of time.

In operation, the test fluid, such as drilling mud, is first placed in chamber 18. Cap 20 is then placed in housing 16 and secured thereto to seal off chamber 18. All lines are connected to the fluid ports of cap 20 and the motor 104 started to impart rotation to shaft 30 at a pre-selected, constant speed. If desired, the filtration unit 10 is heated to a predetermined elevated temperature using heating jacket 11. To control the pressure in chamber 18, valve 108 is opened to allow pressurized gas to flow through conduit 46 and then into chamber 18 to place the test liquid under pressure. At the same time, in the measuring unit 12, piston 142 is positioned such that the cap 144 is against plug 126, i.e. there is no displaced volume in tubular cylinder 120, and chamber 121b is essentially of zero volume. Valve 129 is opened to allow pressurized gas to flow via conduit 127 into chamber 121b. Under these conditions, piston 142 will be held in the undisplaced position by pressure equal to the difference between the pressure in chamber 18 and the pressure in piston chamber 121a exerted by pressurized gas from line 127. It will readily be appreciated that this arrangement permits virtually unlimited control of the differential pressure across the wall 69 of the filter medium cell. Since the pressure in chamber 18 will always be greater than the pressure in chamber 121, and depending upon the permeability of the filter medium, the nature of the test fluid, etc., fluid will flow through the permeable filter medium out of chamber 18 via the clearance or annulus 92 between shaft 30 and the radially inner surface 72 of filter cell 68. The fluid will then pass into chamber 90, through tube 60, will exit the measuring unit 10 via port 56 and line 14 through open valve 16 and finally through port 128 in plug 126 into chamber 121b adjacent end 122. Liquid entering chamber 121b will displace piston assembly 142 away from end 122 toward end 124. As this occurs, the resistance along coil 164 changes as a function of volume of filtrate being accumulated in the chamber 121b. This accumulated volume, initially read as a voltage by circuit 210, is then conveniently recorded as volume measurement versus time by recorder 224 on chart paper 226. With these values, flow rate of test fluid through the filter medium can be easily computed.

In the event that temperatures in the filtration unit 10 are high, seal cooling water via line 110 and valve 112 is passed through the cap 20 to cool the O-ring seals in carrier 36, the cooling water being vented via port 50.

Once the testing has been completed and if desired, the filter medium in the chamber 18 may be cleaned or back flushed by means of cold purge water via line 116, valve 114 and line 14. In this event, valve 16 is closed so that the cold purge water flows into the chamber 18 via port 56, tube 60, chamber 90 and annulus 92.

The apparatus of the present invention can be used to conduct both static and dynamic measurement of fluid loss and filtration and such measurements may be conducted under widely varying temperature and pressure conditions. The apparatus is particularly useful for conducting dynamic measurements in such a way as to simulate shearing similar to that which a drilling mud would undergo when in actual use in a drilling operation. The annulus 92 simulates the annulus which would exist between a conventional drill string and the wall of a borehole during a drilling operation. As shaft 30 is rotated at any desired rate, the test fluid in the annulus 92 sees a shearing action which is a function of that rotational rate. The shear rate may be varied widely by virture of the fact that not only can the shaft rotational speed be varied but the radial size of the annulus 92 can also be varied by changing the diameter of portion 30a of shaft 30.

Another unique feature of the apparatus of the present invention is that the surfaces of the filter medium which are exposed to the test fluid are oriented in a generally vertical direction. Accordingly, settling out of solids, e.g. filter loss additives in the test fluid, is obviated. This is particularly important in static testing, i.e. when the shearing shaft 30 is not used. Moreover, the generally vertical orientation of the filter medium and its coaxial relationship to the shaft 30 simulates the geometry of an actual well.

The simplified construction allows the filter medium to be changed and made from a variety of materials to simulate downhole formations.

The foregoing disclosure and description of the invention is illustrative and explanatory thereof, and various changes in the size, shape and materials as well as in the details of the illustrated construction may be made within the scope of the appended claims without departing from the spirit of the invention.

What is claimed is:

1. Apparatus for testing fluid loss characteristics of a test fluid under static or dynamic conditions, comprising:
    a filter medium cell, said filter medium cell having a generally vertically disposed, cylindrical wall having an inner surface and an outer surface, at least a portion of said cylindrical wall section being formed of a filter medium;
    means defining a first chamber for said test fluid, said first chamber being in open communication with the inner surface of said cylindrical wall portion;
    means forming a second chamber, said second chamber being in open communication with the outer surface of said cylindrical wall portion;
    a generally vertically disposed, rotatable shaft means, at least a portion of said shaft means being received in said filter medium cell and being generally surrounded by said cylindrical wall section;
    means to rotate said rotatable shaft means;
    means to apply a differential pressure across at least said portion of said cylindrical wall section formed of said filter medium between said first chamber and said second chamber; and
    means to measure the amount of test fluid passing through said portion formed of said filter medium from said first chamber to said second chamber.

2. The apparatus of claim 1 wherein said cylindrical wall section is formed of said filter medium.

3. The apparatus of claim 1 including means to support said filter medium cell, said second chamber being at least partially formed in said means to support said filter medium cell.

4. The apparatus of claim 3 including a housing, said means to support said filter medium cell and said filter medium cell being disposed in said housing, said first chamber being at least partially formed in said housing.

5. The apparatus of claim 4 including means to pressurize the interior of said housing.

6. The apparatus of claim 1 including means to heat said filter medium cell to elevated temperatures.

7. The apparatus of claim 1 including means to apply pressure to said second chamber.

8. The apparatus of claim 1 wherein said means to measure the amount of test fluid passing from said first chamber to said second chamber includes means defining a cylindrical chamber and a piston means slidably disposed in said cylindrical chamber, said means for defining said cylindrical chamber having a first fluid port communicating with one side of said piston means and a second fluid port communicating with the other side of said piston means and there are means to connect said first port to said second chamber.

9. The apparatus of claim 8 including means to apply pressure to said other side of said piston means through said second port.

10. The apparatus of claim 8 wherein a variable electrical resistance path is formed between said piston means and said means forming said cylindrical chamber.

11. The apparatus of claim 10 wherein said resistance path includes a slide wire, said slide wire being carried by said piston means.

* * * * *